United States Patent [19]

Harsanyi et al.

[11] 4,062,850

[45] Dec. 13, 1977

[54] THIAZOLOISOQUINOLINES WITH CORONARY AND RESPIRATORY EFFECTS

[75] Inventors: Kalman Harsanyi; Kalman Takacs; Pal Kiss, all of Budapest; Laszlo Szekeres; Gyula Papp, both of Szeged; Eva Benedek, Gyor, all of Hungary

[73] Assignee: Chinoin Pharmaceutical and Chemical Works Ltd., Budapest, Hungary

[21] Appl. No.: 701,130

[22] Filed: June 30, 1976

Related U.S. Application Data

[63] Continuation-in-part of Ser. No. 473,918, May 28, 1974, Pat. No. 3,979,397.

[30] Foreign Application Priority Data

May 30, 1973 Hungary .............................. CI-1381

[51] Int. Cl.$^2$ .................... C07D 513/04; A61K 31/47
[52] U.S. Cl. ........................ 260/286 R; 260/283 CN; 260/283 R; 260/283 S; 260/287 D; 260/287 CF; 260/288 D; 260/288 CF; 260/289 C; 260/289 D; 424/258
[58] Field of Search ...... 260/283 S, 283 CN, 288 CF, 260/287 CF, 286 R; 424/258

[56] References Cited

U.S. PATENT DOCUMENTS

| 3,042,671 | 7/1962 | Lombardino et al. | ........ 260/288 CF |
| 3,455,933 | 7/1969 | Georgiadis et al. | ................ 260/283 S |
| 3,466,289 | 9/1969 | Osbond et al. | .................... 260/283 S |
| 3,979,397 | 9/1976 | Harsanyi et al. | .................. 260/283 S |

FOREIGN PATENT DOCUMENTS

2,426,267  1/1975  Germany ...................... 260/283 CN

OTHER PUBLICATIONS

Harsanyi et al., Chem. Abs. vol. 82: 156275x (1975) (Abstract of Ger. Off. 2,426,267).

*Primary Examiner*—Donald G. Daus
*Assistant Examiner*—Mary C. Vaughn
*Attorney, Agent, or Firm*—Karl F. Ross

[57] ABSTRACT

1-Cyano-2-imino-2H,4H-5,6-dihydro-8,9-dimethoxy-1,2-thiazolo(3,2a)isoquinoline or 2-imino-2H,4H-5,6-dihydro-8,9-dimethoxy-1,2-thiazolo(3,2a)isoquinoline or a pharmaceutically acceptable salt thereof. These compounds are effective as heart medicines and respiratory analeptics.

3 Claims, No Drawings

THIAZOLOISOQUINOLINES WITH CORONARY AND RESPIRATORY EFFECTS

This application is a continuation in part of Ser. No. 473,918, filed May 28, 1974, now U.S. Pat. No. 3,979,397 issued Sept. 7, 1976.

This invention relates to new sulfur-containing heterocyclic compounds the same, as well as to a process for the preparation thereof.

The structure of the new sulfur-containing heterocyclic compounds, termed thereafter briefly as "thiazoloisoquinolines" is given by formula along with the numbering of the ring system.

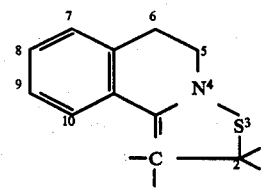

(XIII)

As shown by the above formula, the new ring system encompasses condensed heterocycles.

The 2H,4H-1,2-thiazolo[3,2-a]isoquinolines shown in formula (XIII) contain a 1,2-thiazole ring condensed with the isoquinoline ring system. These compounds are termed thereafter briefly as "1,2-thiazoloisoquinolines". In these compounds the carbon atom in position 2, with two free valences, is in an oxidation state of 3, i.e. is a $C^2$ carboxylic acid derivative.

The general symbols used in the specification and the claims to define the individual substituents have the following meanings:

$R^1$ is hydrogen, hydroxy, alkoxy or aralkoxy,
$R^2$ is hydrogen, hydroxy, alkoxy or aralkoxy,
$R^3$ is hydrogen, cyano, alkyl, aryl, nitro, carboxy, carboalkoxy or carboxamido,
$R^4$ is hydrogen, alkyl, aryl, acyl, alkylsulfonyl or arylsuflonyl,
$R^5$ is hydrogen, hydroxy, alkoxy or aralkoxy,
$R^6$ is hydrogen, hydroxy, alkoxy or aralkoxy,
$R^7$ is hydrogen, cyano, alkyl, aryl, carboxy, carboalkoxy or carboxamido,
$R^8$ is hydrogen, alkyl, aryl, acyl, alkylsulfonyl or arylsulfonyl,
X is hydrogen, halogen or mercapto,
Y is oxygen, sulfur or =N—$R^4$, and
Y' is oxygen, sulfur or =N—$R^8$.

Where $R^1$ and $R^2$ are alkoxy or aralkoxy, the alkoxy contains from 1 to 6 and preferably from 1 to 4 carbon atoms. The aryl included in the aralkoxy moiety is either phenyl, 1- or 2-naphthyl, or phenyl or naphthyl substituted by halo selected from the group consisting of chloro, bromo and iodo, the alkyl of this moiety being $C_1$ to $C_6$, preferably $C_1$ to $C_4$. Where $R^3$ is alkyl it contains from 1 to 6 and preferably from 1 to 4 carbons, where $R^3$ is aryl that includes phenyl, 1- or 2-naphthyl, or phenyl or naphthyl substituted by halo selected from the group which consists of chloro, bromo and iodo; where $R^3$ is carboalkoxy, the alkoxy contains from 1 to 6 and preferably from 1 to 4 carbon atoms, and where $R^3$ is carboxamido, the carboxamido is unsubstituted or the nitrogen atom thereon is mono or disubstituted by alkyl containing from 1 to 6 and preferably from 1 to 4 carbon atoms. Where Y is =N—$R^4$ and $R^4$ is alkyl, the alkyl contains from 1 to 6 and preferably from 1 to 4 carbon atoms, where $R^4$ is aryl, the aryl is either phenyl, 1- or 2-naphthyl or phenyl or naphthyl substituted by halo selected from the group which consists of chloro, bromo and iodo, where $R^4$ is acyl the acyl group contains from 1 to 6 and preferably 1 to 4 carbon atoms or the acyl is benzoyl or benzoyl substituted by at least one halogen selected from the group consisting of chlorine, bromine and iodine and finally where $R^4$ is alkylsulfonyl or arylsulfonyl, the alkyl and aryl groups are as defined above.

Where $R^5$ and $R^6$ are alkoxy or aralkoxy, the alkoxy contains from 1 to 6 and preferably from 1 to 4 carbon atoms. The aryl included in the aralkoxy moiety is either phenyl, 1 or 2-naphthyl, or phenyl or naphthyl substituted by halo selected from the group consisting of chloro, bromo and iodo, the alkyl of this moiety containing from 1 to 6 and preferably 1 to 4 carbon atoms. Where $R^7$ is alkyl it contains from 1 to 6 and preferably from 1 to 4 carbon atoms, where $R^7$ is aryl that includes phenyl, 1- or 2-naphthyl, or phenyl or naphthyl substituted by halo selected from the group consisting of chloro, bromo and iodo, where $R^7$ is carboalkoxy, the alkoxy contains from 1 to 6 and preferably from 1 to 4 carbon atoms, and where $R^7$ is carboxamido, the carboxamido is unsubstituted or the nitrogen atom thereon is mono or disubstituted by alkyl containing from 1 to 6 and preferably from 1 to 4 carbon atoms. Where $R^8$ is alkyl, the alkyl contains from 1 to 6 and preferably from 1 to 4 carbon atoms, where $R^8$ is aryl, the aryl is either phenyl, 1- or 2-naphthyl or phenyl or naphthyl substituted by halo selected from the group consisting of chloro, bromo and iodo, where $R^8$ is acyl, the acyl group contains from 1 to 6 and preferably 1 to 4 carbon atoms or the acyl is benzoyl or benzoyl substituted by at least one halogen atom selected from the group consisting of chlorine, bromine and iodine and where $R^8$ is alkylsulfonyl or arylsulfonyl, the alkyl and aryl groups are as defined above. Finally, where X is halo, the halo is fluoro, chloro, bromo or iodo.

This invention relates to new thiazoloisoquinolines of the formula (I).

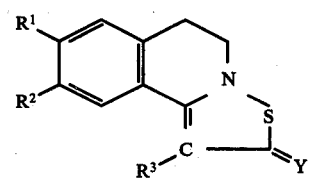

(I)

wherein the symbols have the meanings defined above. This invention relates further to pharmaceutical products containing as active ingredient these new compounds, as well as to a process for the preparation of active ingredients.

The compounds of the general formula can be prepared according to the invention by reacting a compound of the formula

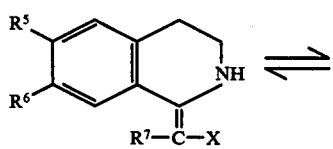

(II)

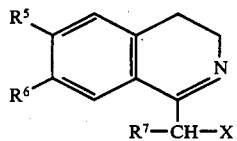

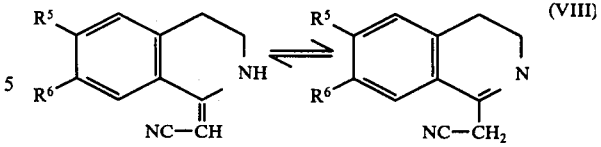

wherein the symbols have the meanings defined above, or a salt thereof with a reactive carbonic acid derivative, provided that at least one of the reactants contains a sulfur atom, and/or by oxidizing an isoquinoline derivative of the formula (III)

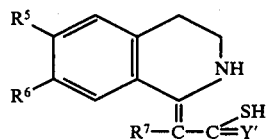

wherein the symbols have the meanings defined above, and/or by converting substituents A', $R^5$, $R^6$ and $R^7$ of the obtained thiazoloisoquinolines of the formula (IA)

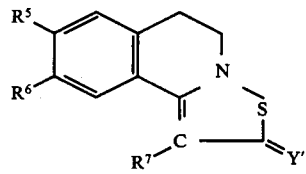

into those required in the end-products. If desired, the obtained thiazoloisoquinolines are converted into their salts, or the compounds of the formula (I) are liberated from the corresponding salts.

The compounds of the formula (I) can be used primarily as pharmaceuticals or intermediates in the production of pharmaceutically active substances. Members of this group exert a very favorable action on the heart musculature, pulmonary circulation and on the oxygen consumption of the heart musculature. The toxicity of these compounds is low. Accordingly, the compounds having the formula (I) can be used in practice as heart medicines and respiratory analeptics.

As shown by formulae (II), (IV), (VI), (VII) and (VIII),

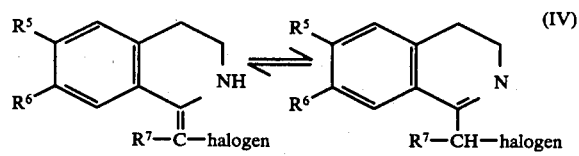

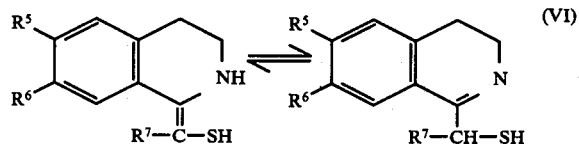

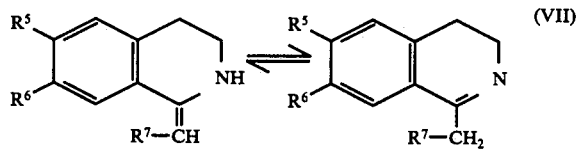

all compounds of these groups may exist in at least two tautomeric forms. The scope of the invention extends to all of these tautomers and tautomeric mixtures.

The carbonic acid-type reagent is chosen according to the substituent of the side chain attached to position 1 of the isoquinoline having the formula (II), and according to the substituent required in position 3 of the condensed ring system of the intermediate having the formula (IA). Thus, e.g. rhodanides, halocyanides, mono-thiocarbonic acid esters, thioureas, xanthates, cyanamides, acylisothiocyanates, carbon disulfide, etc. can be used as carbonic acid-type reagent. If desired, these reagents can be formed directly in the reaction medium from the appropriate precursors.

According to one method of the invention an isoquinoline of the formula (IV), i.e. a compound containing a halogen-substituted side chain in position 1, is used as starting substance. This compound can be reacted with carbonic acid derivatives in various ways, to yield the compounds of the formula (IA) either directly or via one or more other intermediates.

The reaction is carried out preferably in an alcohol or in another protic solvent, such as a formamide. As solvents, however, dipolar aprotic substances, e.g. dimethylformamide, dimethylsulfoxide, or hexamethylphosphoric acid triamide can also be used.

The reaction temperature is adjusted in accordance with the solvent used. If a solvent with a boiling point lower than 100° C is used as the reaction medium, the reaction is carried out at the boiling point of the system whereas when solvents of higher boiling points are used, the reaction temperature is between 80° and 120° C.

The products can be separated in crystalline form from the solvent, using optionally another solvent as precipitant.

As starting substances of the formula (IV) the ones containing a bromine substituent in the side chain are utilized preferably. These compounds can be prepared easily by the bromination of the appropriately substituted 1-methylene-1,2,3,4-tetrahydroisoquinolines. According to a preferred method of the invention the obtained isoquinoline derivative containing a halogen-substituted side chain is reacted further directly in the medium where it has been prepared, i.e. without isolation.

When reacting isoquinolines of the formula (IV) with other sulfur-containing carbonic acid derivatives, sulfur-containing isoquinoline intermediates of the formulae (III) or (VI) are obtained in one or more steps.

Thus, the salts of the mercapto-isoquinolines of the formula (VI) can be prepared by reacting an isoquinoline of the formula (IV) with thiourea, and decomposing the obtained isothiuronium salt with an alkali. The obtained mercaptides represent a subgroup of the starting substances having the formula (II), offering subsequent reactions described below.

When reacting the compounds of the formula (IV) with sodium thiosulfate, again isoquinolines of the general formula (VI) are obtained via the appropriate Bunte's salts.

The conditions of these reactions depend on the reactants utilized. The reactants are generally given to the aqueous solution of the appropriate alkali metal salt of the thiolate. If the hydrolyzability of the reactant does not permit carrying out the reaction in an alkaline medium, the reaction is carried out in a well stirred two-phase system. As water-immiscible solvents, preferably hydrocarbons or chlorinated organic solvents are used. In other cases dipolar aprotic solvents, e.g. dimethylformamide can be used to advantage. The reactions are in general carried out at low temperatures.

Similarly, the end-products can be obtained via intermediates by reacting the compounds of the formula (IV), in the form of the corresponding Grignard-reagents, with carbon disulfide. The Grignard-reagent can be prepared in ether-type solvents, such as in diethyl ether, dioxane or tetrahydrofuran.

According to a further method of the invention isoquinolines of the formula (VII), constituting a subgroup of the compounds having the formula (II), are used as starting subtances. These compounds can be reacted with sulfur-containing carbonic acid derivatives to yield the sulfur-containing isoquinolines, optionally via one or more intermediates.

Thus, for instance, the compounds of the formula (VII) can be reacted with acylisothiocyanates to yield the corresponding isoquinolines containing an N-acylimino substituent in the side chain. The acyl group of these substances can be split off, if desired. These acylated or deacylated intermediates can be used for the preparation of 1,2-thiazoloisoquinolines containing an imino or =N-acyl substituent in position 2 of the condensed ring system. In this latter case the acyl substituent attached to the nitrogen atom may be benzoyl, alkylsulfonyl or arylsulfonyl group.

The reaction with acylisothiocyanates is carried out preferably in acetone, chlorinated solvents, ketones, lower nitriles, ethers, etc.

According to a still further method of the invention the isoquinolines of the formula VIII (R³ = cyano or nitrile), containing a cyanomethylene side chain and constituting a subgroup of the compounds having the formula (VII), are reacted with hydrogen sulfide to yield the thiocarbamoyl-substituted intermediates of the formula (IX).

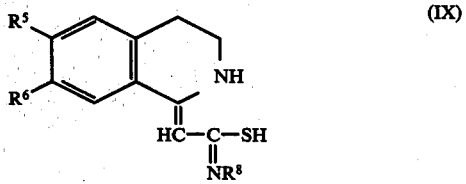
(IX)

These latter compounds can be oxidized to yield the corresponding 1,2-thiazoloisoquinolines. The reaction with hydrogen sulfide is carried out preferably by introducing hydrogen sulfide gas into the system at 0° to 50° C, in the presence of a basic substance, e.g. triethylamine, piperidine or, preferably, pyridine. The addition of hydrogen sulfide can be speeded up by the use of higher temperature in a closed vessel.

By reacting the compounds of the formula (VII) with ethyl magnesium bromide, a trans-Grignard reaction can also be carried out. During this reaction ethane is evolved, which is removed from the system by heating. The reaction is carried out preferably in toluene, in the presence of a small amount of ether. The reaction of the obtained reagent with carbon disulfide also leads to the intermediates of the formula (III), containing a dithiocarboxy substituent in the side chain.

The compounds of the formula (VII) that contain a carbonylchloride substituent in the side chain can be converted into the isoquinolines of the formula (X) in a reaction with sodium hydrosulfide.

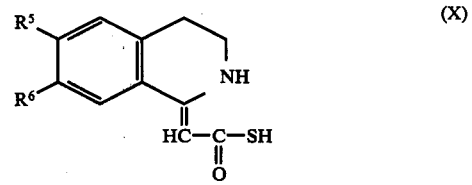
(X)

The compounds of the formula (X), containing a thiocarboxy substituent in the side chain, constitute a subgroup of the compounds having the formula (III).

The isoquinolines of the formula (III) can be oxidized into the 1,2-thiazoloisoquinoline end-products.

The oxidation can be carried out preferably with a halogen in the presence of an acid binding agent. Thus, for example, the reaction can be carried out with iodine or bromine in the presence of pyridine, quinoline, picoline, lutidine, etc. The reaction is in general conducted at about 50° C.

It is obvious to one skilled in the art that the carbonic acid derivatives used as reactants are selected generally in accordance with the desired substituents of the 1,2-thiazoloisoquinoline end-products.

Once the thiazoloisoquinoline ring system is built up, the substituent groups introduced during ring closure can be converted into other groups, and thus the compounds of the formula (IA) can be converted into the compounds of the formula (I).

Thus, for example, the hydroxy groups attached to positions 8 and 9, respectively, can be alkylated or aralkylated, or the alkoxy or aralkoxy groups can be converted into hydroxy substituents. The ether bond can be split by hydrogen halides, pyridine hydrochloride, etc. Alkoxy- and aralkoxy groups can be formed by reacting the hydroxy compounds with appropriate alkyl or aralkyl halides or sulfates in the presence of an acid binding agent. The ether bond of the benzyloxy derivatives can also be split by catalytic hydrogenation. In the alkoxy or aralkoxy groups the alkyl chain may contain preferably 1 to 4 carbon atoms, and the most preferred aralkyl group is benzyl.

The thiazoloisoquinolines containing a side-chain in position 1 to which a group derived from a carbonic acid is attached can be converted into the corresponding compounds containing a carboxy substituent in the side chain.

The nitrile group in position 1 of the ring system can be converted into an acid amide or carboxy group by treatment with an acid. In this reaction preferably sulfuric acid is applied. The nitrile group in position 1 can also be converted into carboxy group by treatment with a base. Alternately, the nitrile group can be converted into a carbalkoxy group by acid-catalyzed alcoholysis. In turn, the acid amide group can be dehydrated with phosphorous pentoxide, phosphorous oxychloride or thionyl chloride to yield the corresponding nitrile-substituted compounds. The nitrile group can also be converted into an acid amide group by treatment with a concentrated acid (e.g. sulfuric or polyphosphoric acid) or with an alkaline hydrogen peroxide solution.

The compounds that contain a carboxy group in position 1 of the condensed ring system can be esterified with alcohols in proton-catalyzed reactions. Alternately, these compounds can be decarboxylated by heating.

The compounds wherein the side chain attached to position 1 of the ring system contains a methyl group can be converted into the corresponding carboxy substituted compounds by oxidation with potassium permanganate. The imino groups attached to position 2 of the condensed ring system can be alkylated with known alkylating agents, preferably after salt-formation with a strong base. For this purpose e.g. sodium alcoholates, sodium amide or sodium hydride can be used. N-acylation can be carried out in pyridine medium with various acylating agents, e.g. carboxylic chlorides, aryl or acylsulfonic acid chlorides. etc. The acyl group of the N-acylimino groups attached to position 2 of the condensed ring system can be removed by acid hydrolysis.

The condensed-ring compounds containing an imino group can be reacted with amine salts to yield the corresponding N-substituted derivatives. This reaction is carried out preferably in dimethylformamide, at the boiling point of the solvent.

The basic compounds of the formula (I) can be converted into their salts by reacting them with mineral or organic acids, e.g. sulfuric, hydrochloric, phosphoric, nitric, acetic, rhodanic, propionic, lactic, malic, citric, succinic, maleic, fumaric, ethanedisulfonic, benzoic, salicylic, aspartic, etc. acids. Using polybasic acids, acidic salts can be formed as well.

The compounds of the formula (I) can be converted into pharmaceutical products, e.g. tablets, coated tablets, suppositories, capsules, solutions, powders, injectable preparations, etc. These compositions may contain the active agents as such, or in admixture with carriers, diluents and/or other additives.

EXAMPLE 1

A methanol solution of 0.8 g. (0.01 moles) of bromine is added dropwise, at 30°–40° C, to the solution of 1.45 g. (0.005 moles) of 1-($\alpha$thiocarbamoyl)-cyanomethylene-1,2,3,4-tetrahydro-6,7-dimethoxy-isoquinoline in 25 ml. of dry pyridine. The mixture is stirred for one hour at the same temperature, thereafter cooled to room temperature, and the separated product is filtered by suction. 1.1 g. of 1-cyano-2-imino-2H,4H-5,6-dihydro-8,9-dimethoxy-1,2-thiazolo[3,2-a]isoquinoline hydrobromide are obtained; m.p.: 276°–277° C under decomposition (after recrystallization from 50% ethanol).

Analysis: Calculated for $C_{14}H_{14}N_3O_2Brs$ (M=368.26): C: 45.65% H: 3.83% N: 11.41% Br: 21.97% S: 8.71% Found: C: 45.88% H: 3.78% N: 11.66% Br: 22.05% S: 9.02%.

EXAMPLE 2

To a solution of 1.32 G (0.005 moles) of $\alpha$-(6,7-dimethoxy-3,4-dihydro-1-isoquinolyl)-thioacetamide and 25 ml of pyridine, 0.8 g (0.01 mole) of bromine in 5 ml. of methanol are added under stirring at 28°–30° C. The reaction mixture is stirred at this temperature for a further hour and evaporated in vacuo. The residue is crystallized from anhydrous ethanol. Thus 0.8 g. of 2-imino-2H,4H-5,6-dihydro-8,9-dimethoxy-1,2-thiazolo[3,2-a]isoquinoline-hydrobromide are obtained. Mp.: 194°–195° C (decomposition).

Analysis for the formula $C_{13}H_{14}N_2O_2Brs$ calc.: C%=45.62; H%=4.12; N%=8.18; Br%=23.34; S%=9.36. found: C%=45.35; H%=4.2; N%=8.1; Br%=23.45; S%=9.45.

We claim:
1. 1-cyano-2-imino-2H, 4H -5,6-dihydro-8,9-dimethoxy-1,2-thiazolo(3,2a) isoquinoline or 2-imino-2H,4H-5,6-dihydro-8,9-dimethoxy-1,2-thiazolo(3,2a) isoquinoline or a pharmaceutically acceptable salt thereof.
2. The compound defined in claim 1 which is 1-cyano-2-imino-2H,4H-5,6-dihydro-8,9-dimethoxy-1,2-thiazolo[3,2-a]isoquinoline hydrochloride.
3. The compound defined in claim 1 which is 2-imino-2H,4H-5,6-dihydro-8,9-dimethoxy-1,2-thiazolo[3,2-a]isoquinoline hydrobromide.

* * * * *